(12) United States Patent
Horsager et al.

(10) Patent No.: US 8,311,634 B2
(45) Date of Patent: *Nov. 13, 2012

(54) APPARATUS AND METHOD FOR ELECTRICAL STIMULATION OF HUMAN RETINA

(75) Inventors: Alan Matthew Horsager, Los Angeles, CA (US); Scott H. Greenwald, Seattle, WA (US); Mark S. Humayun, Glendale, CA (US); Matthew J. McMahon, Los Angeles, CA (US); Ione Fine, Seattle, WA (US); Robert J. Greenberg, Los Angeles, CA (US); Geoffrey M. Boynton, Seattle, WA (US)

(73) Assignee: Second Sight Medical Products Inc., Sylmar, CA (US)

( * ) Notice: Subject to any disclaimer, the term of this patent is extended or adjusted under 35 U.S.C. 154(b) by 759 days.

This patent is subject to a terminal disclaimer.

(21) Appl. No.: 11/818,373

(22) Filed: Jun. 14, 2007

(65) Prior Publication Data

US 2008/0021515 A1     Jan. 24, 2008

Related U.S. Application Data

(60) Provisional application No. 60/814,308, filed on Jun. 16, 2006.

(51) Int. Cl.
*A61N 1/08* (2006.01)
(52) U.S. Cl. .......................... 607/54; 607/53
(58) Field of Classification Search .................. 607/53, 607/54, 115
See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,052,024 A * | 9/1991 | Moran et al. | 375/219 |
| 5,109,844 A | 5/1992 | de Juan, Jr. et al. | |
| 5,166,749 A * | 11/1992 | Curbelo et al. | 356/452 |
| 5,215,088 A | 6/1993 | Normann et al. | |
| 5,935,155 A | 8/1999 | Humayun et al. | |
| 5,944,747 A | 8/1999 | Greenberg et al. | |
| 6,400,989 B1 | 6/2002 | Eckmiller | |
| 6,442,431 B1 * | 8/2002 | Veraart et al. | 607/54 |
| 6,458,157 B1 | 10/2002 | Suaning | |
| 6,658,299 B1 * | 12/2003 | Dobelle | 607/54 |
| 6,718,209 B2 | 4/2004 | Williamson et al. | |

(Continued)

FOREIGN PATENT DOCUMENTS

WO    WO 00/56393    9/2000

(Continued)

OTHER PUBLICATIONS

Donaldson, Gail S. et al. "Psyhcometric functions and temporal integration in electric hearing." J. Acoustic Soc. Am. 101 (6), Jun. 1997. pp. 3706-3721.*

(Continued)

*Primary Examiner* — Carl H Layno
*Assistant Examiner* — Allen Porter, Jr.
(74) *Attorney, Agent, or Firm* — Scott B. Dunbar; Alessandre Steinfl

(57) ABSTRACT

An apparatus and method for retinal stimulation are shown. The method comprises varied parameters, including frequency, pulse width, and pattern of pulse trains to determine a stimulation pattern and visual perception threshold.

26 Claims, 15 Drawing Sheets

U.S. PATENT DOCUMENTS

| | | | |
|---|---|---|---|
| 6,745,155 B1 * | 6/2004 | Andringa et al. | 702/189 |
| 6,974,533 B2 | 12/2005 | Zhou | |
| 7,003,355 B1 * | 2/2006 | Suaning et al. | 607/54 |
| 2003/0181957 A1 * | 9/2003 | Greenberg et al. | 607/54 |
| 2004/0127957 A1 * | 7/2004 | Fujikado et al. | 607/54 |
| 2004/0176821 A1 | 9/2004 | Delbeke et al. | |
| 2004/0236389 A1 | 11/2004 | Fink et al. | |
| 2005/0055069 A1 * | 3/2005 | Franck | 607/62 |
| 2005/0222624 A1 | 10/2005 | Greenberg et al. | |
| 2005/0228647 A1 * | 10/2005 | Fisher | 704/205 |
| 2006/0129207 A1 | 6/2006 | Fried et al. | |
| 2007/0142877 A1 * | 6/2007 | McLean | 607/54 |

FOREIGN PATENT DOCUMENTS

| | | | |
|---|---|---|---|
| WO | WO 03/076011 A1 | 9/2003 | |

OTHER PUBLICATIONS

De Juan, E., et al. Retinal Tacks, American Journal of Ophthalmology 99: pp. 272-274, Mar. 1985.

Chander, D., E. J. Chichilnisky, Adaption to Temporal Contrast in Primate and Salamander Retina, The Journal of Neuroscience, vol. 21(24): pp. 9904-9916, Dec. 2001.

Kim, J. K., F. Rieke, Temporal Contrast Adaptation in the Input and Output Signals of Salamander Retinal Gaglion Cells, The Journal of Neuroscience, vol. 21(1): pp. 287-299, Jan. 2001.

Baccus, S. A., M. Meister, Fast and Slow Contrast Adaptation in Retinal Circuitry, Neuron, vol. 36: pp. 909-919, Dec. 2002.

Jensen, R. J., O. R. Ziv, et al., Thresholds for Activation of Rabbit Retinal Ganglion Cells with Relatively Large, Extracellular Microelectrodes, Investigative Opthalmology & Visual Science, vol. 46, No. 4: pp. 1486-1496, Apr. 2005.

Kandel, E. R., J. H. Schwartz, et al., Principals if Neural Science; Fourth Edition, pp. 125-149, 2000.

Fried, S. I., H., A. Hsueh, et al., A Method for Generating Precise Temporal Patters of Retinal Spiking Using Prosthetic Stimulation, J Neurophysiol, vol. 95: pp. 970-978, Feb. 2006.

O'Brien, B. J., T. Isayama, et al., Intrinsic Physiological Properties of Cat Retinal Ganglion Cells, Journal of Physiology, 5383.3: pp. 787-802, 2002.

* cited by examiner

IN EACH TRIAL  PRESENTED.

Q: DID YOU SEE STIMULUS? (YES/NO)

APPARATUS AND METHOD FOR ELECTRICAL STIMULATION OF HUMAN RETINA

CROSS REFERENCE TO RELATED APPLICATIONS

This application claims priority to U.S. Provisional Ser. No. 60/814,308 for "Human Retinal Electrical Stimulation Using Pulse Trains" filed on Jun. 16, 2006, which is incorporated herein by reference in its entirety.

GOVERNMENT RIGHTS NOTICE

This invention was made with government support under grant No. R24EY12893-01, awarded by the National Institutes of Health. The government has certain rights in the invention.

FIELD

The present disclosure is generally directed to neural stimulation and more specifically to an apparatus and method for providing intensity control.

BACKGROUND

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., de Juan, et al., 99 Am. J. Opthalmol. 272 (1985). These retinal tacks have proved to be biocompatible and remain embedded in the retina, with the choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY

The present disclosure relates to an apparatus and method for retinal stimulation wherein the apparatus allows for the placement of a prosthetic device on the inner retinal surface to provide artificial sensations including vision; and wherein visual perception threshold is determined and stimulation parameters are varied, including frequency, pulse width, and pattern of pulse trains.

According to a first embodiment of the present disclosure, a retinal stimulation method is provided, comprising: generating a stimulation pattern by stimulating a retina of a patient with an impulsive electrical signal; and determining how visual perception depends on the generated stimulation pattern by observing perceptual threshold as a function of features of the impulsive electrical signal.

According to a second embodiment of the present disclosure, a method for determining visual perceptual threshold is provided, comprising: exposing subjects to a series of variable current stimuli; decreasing amplitude of the variable current stimuli if subject answers correctly to a current stimulus; increasing amplitude of the current stimuli if subject answers incorrectly to the current stimulus; and generating a psychometric function based on answers of the subject, wherein a yes-no paradigm is used, and half of the series of variable current stimuli contained no stimulus.

According to a third embodiment of the present disclosure, a method for determining visual perceptual threshold is provided, comprising: exposing subjects to a series of variable current stimuli; decreasing amplitude of the variable current stimuli if subject answers correctly to a current stimulus; increasing amplitude of the current stimuli if subject answers incorrectly to the current stimulus; and generating a psychometric function based on answers of the subject, wherein the variable current stimuli are varied in a 3 up-1 down staircase pattern.

According to a fourth embodiment of the present disclosure, a retinal stimulation apparatus is provided, comprising: means for generating a stimulation pattern by stimulating a retina of a patient with an impulsive electrical signal; and means for determining how visual perception depends on the generated stimulation pattern by observing perceptual threshold as a function of features of the impulsive electrical signal.

According to a fifth embodiment of the present disclosure, a visual prosthetic apparatus for retinal stimulation is provided comprising an implantable portion and an external portion, wherein the implantable portion comprises a cable, an RF receiver, an inductive coil and an array of electrodes, for stimulating visual neurons, and the external portion comprises a frame, a camera, an external coil and a mounting system for the external coil.

According to a sixth embodiment of the present disclosure, a retinal stimulation device is provided, comprising: a stimulation pattern generator to provide a signal to a retina, wherein the stimulation pattern generator generates an impulsive electrical signal comprising a pulse train of biphasic pulses, the pulse train having a delay between pulses and a pulse train frequency.

According to a further embodiment of the present disclosure, an apparatus or device for performing any of the method claims of the present disclosure, alone or in combination, is disclosed.

Further embodiments are disclosed throughout the specification, drawings and claims of the present disclosure.

DETAILED DESCRIPTION

Figure 1:
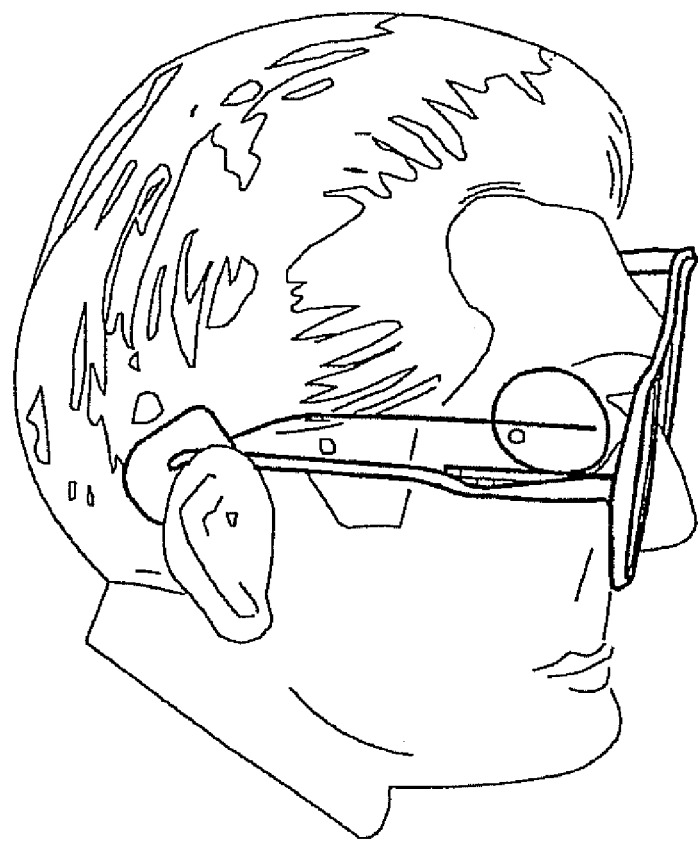
FIG. 1 is a brief schematic view of an implanted visual prosthesis.

FIG. 1 is a schematic view of a prosthesis for stimulating retinal cells. Patients suffering from retinitis pigmentosa (RP) sustain severe vision loss as a result of photoreceptor death.

Figure 2:
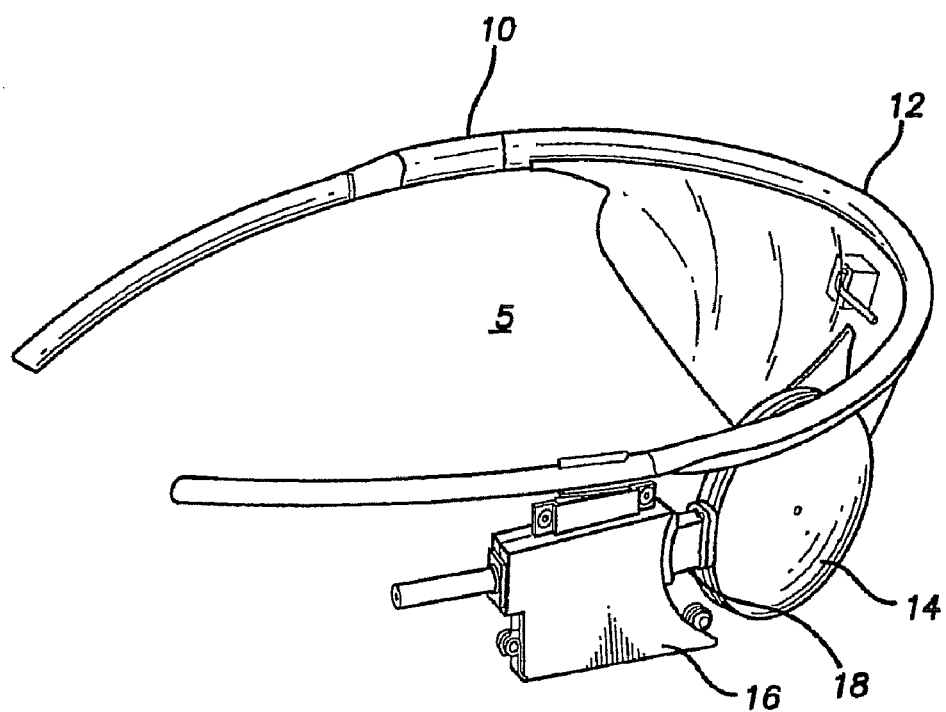
FIG. 2 is a prospective view of a visual prosthesis.
Figure 3:
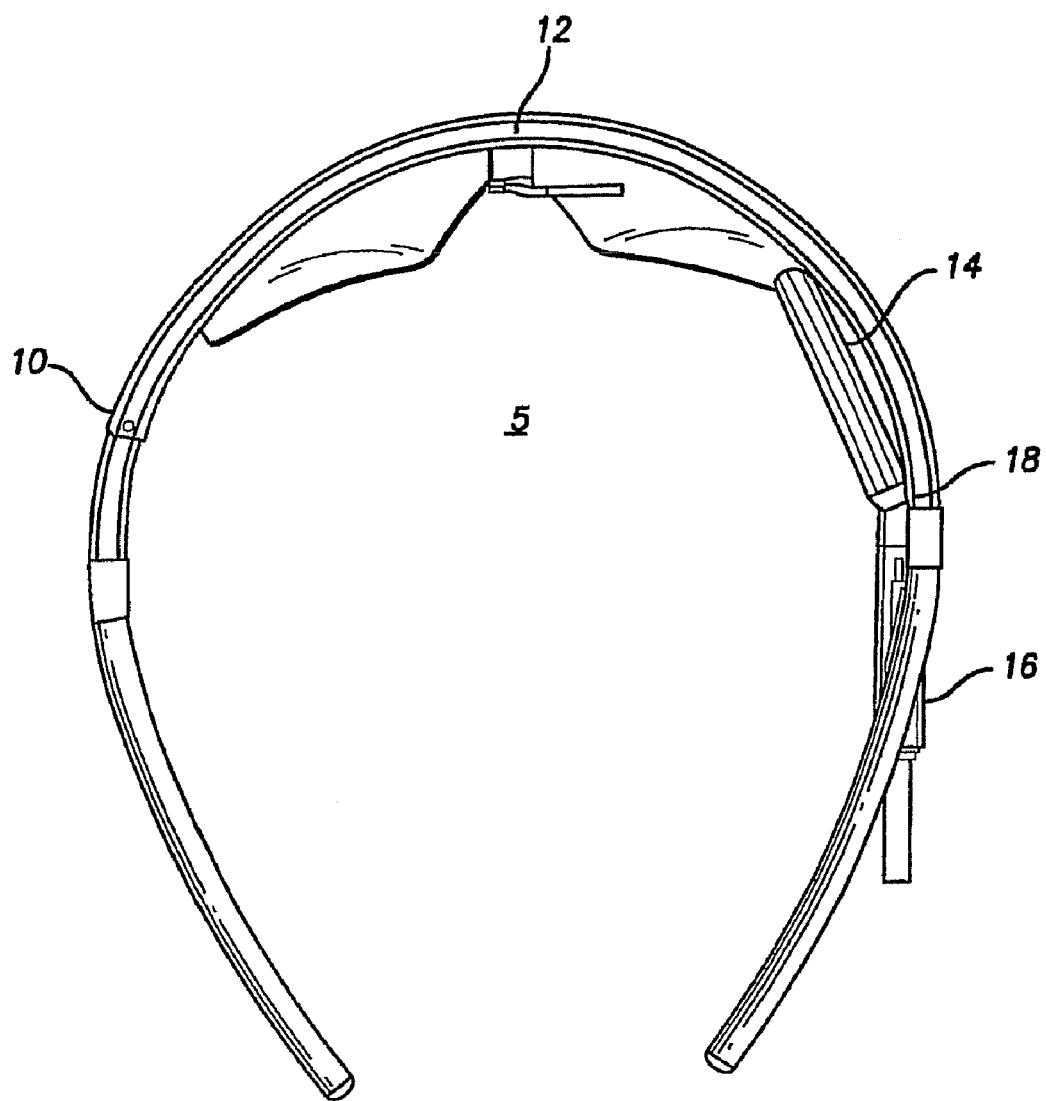
FIG. 3 is a top view of the visual prosthesis shown in FIG. 2.
Figure 4:
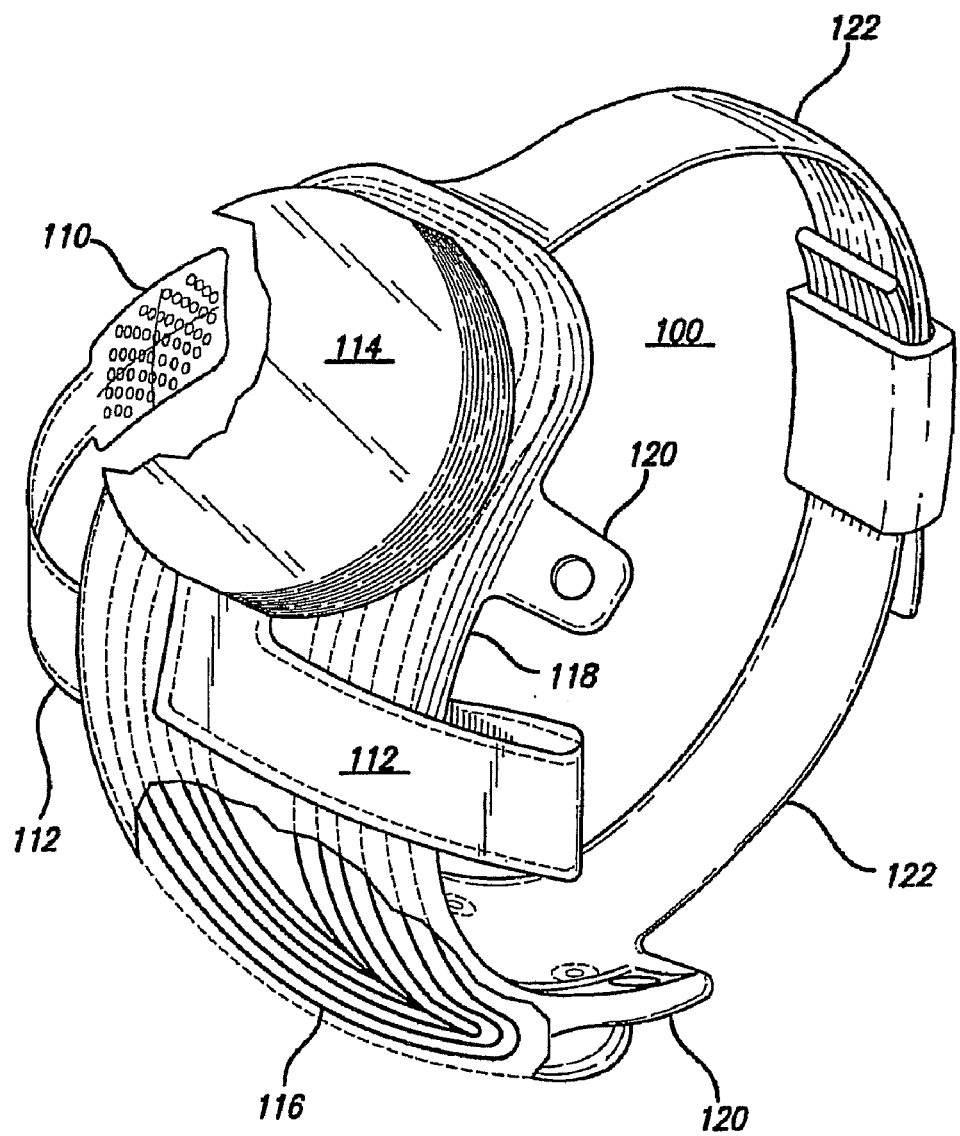
FIG. 4 is a perspective view of the implantable portion of a visual prosthesis.
Figure 5:
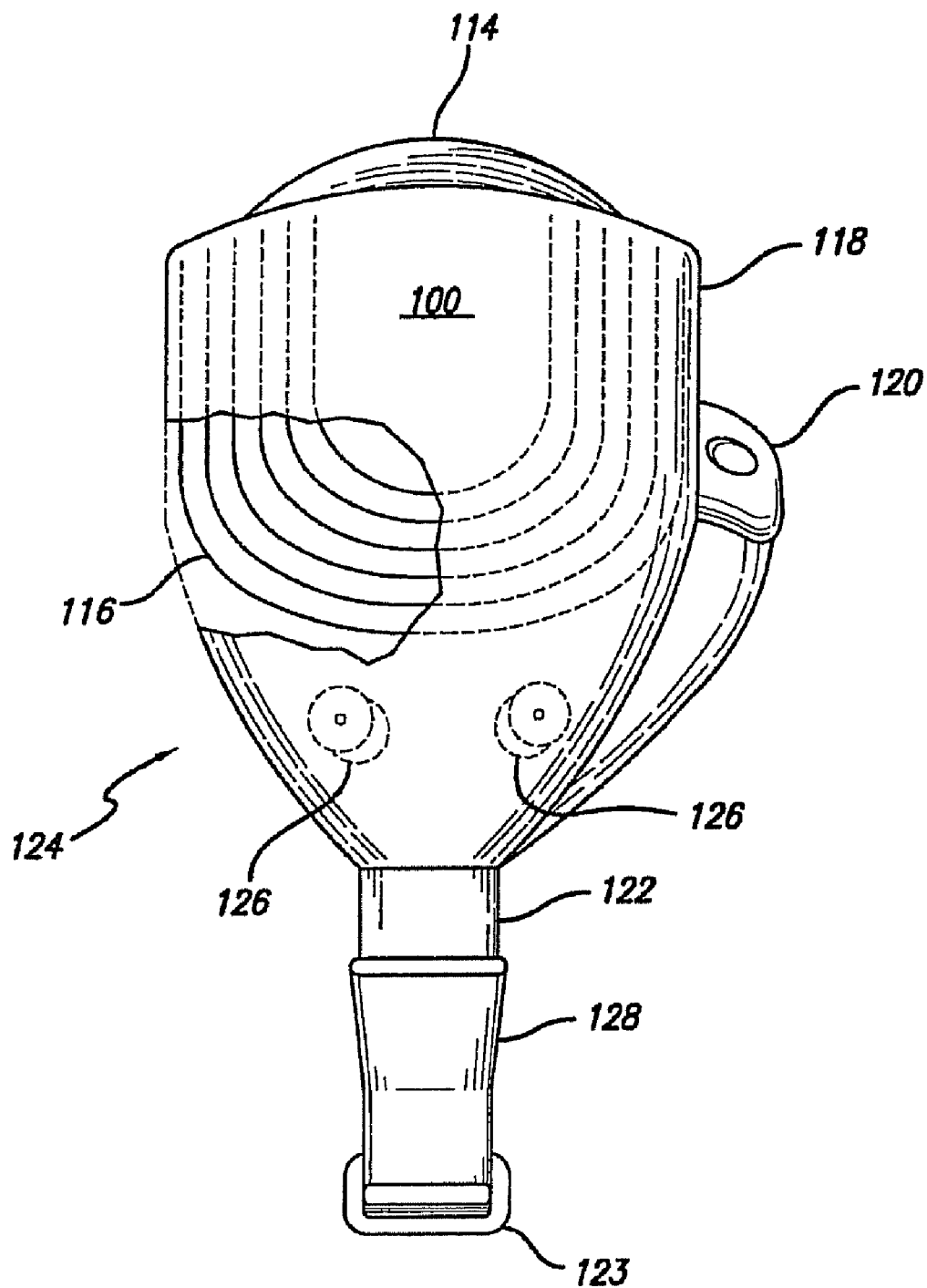
FIG. 5 is a side view of the implantable portion of a visual prosthesis showing the fan tail in more detail.

FIGS. 2 and 3 show two different perspective views of a visual prosthesis apparatus according to the present disclosure. The visual apparatus provides an implantable portion 100 and an external portion 5. Portion 5 is shown in FIGS. 2 and 3. Portion 100 is shown in FIGS. 4 and 5. The external portion 5 comprises a frame 10 holding a camera 12, an external coil 14 and a mounting system 16 for the external coil 14. The mounting system 16 also encloses the RF circuitry.

Three structural features are provided in the visual prosthesis to control the distance, and thereby reduce the distance, between the external coil 14 and the inductive (internal) coil (116, FIG. 4). The three structural features correspond to movement of the external coil along the three possible spatial axes occupied by the two coils. That is, the external and inductive coils can be viewed as being separated in anatomical axes: the medial-lateral, superior-inferior, and the anterior-posterior axis.

In this way, the first structural feature reduces the distance between the coils along the medial-lateral axis by bending the external coil 14. The distance in this medial-lateral axis should be equivalent to the separation distance of the coils if the centers of the coils are aligned. The enclosure of the external coil 14 is attached to the mounting system 16, which is attached to the leg frame 10 of the visual apparatus. While the RF circuitry within the mounting system 16 is in line with the leg frame, the external coil has been given a preferential bend 18 towards the face using a flexible connector. With the external coil 14 angled toward the face (e.g. at 25 degrees) (see FIGS. 2 and 3), the external coil 14 makes contact with the subject's face and the flexible connector allows conformation to the subject's facial contours. Thus, the external coil 14 is brought in as close as possible in the medial-lateral axis for the subject.

The second structural feature is a sliding bar mechanism controlling movement along the anterior-posterior axis. The point at which the mounting system 16 connects to the visor allows for 7 mm of adjustment along this anterior-posterior axis. The sliding bar mechanism can be fixed in place when the optimal position is found by tightening two screws on the sides of the sliding bar.

The third structural feature is adjustment of the visual apparatus along the superior-inferior axis by varying the placement of the visual apparatus along the subject's nose. When the visual apparatus is worn close to the face, the external coil 14 is higher, and when worn further from the face, the external coil 14 is lower. Using these three structural adjustments in combination, the coil separation distance can be adjusted to obtain an optimal RF link for individual subjects.

FIG. 4 shows a perspective view of an implantable portion 100 of a retinal prosthesis as disclosed. An electrode array 110 is mounted by a retinal tack or similar means to the epiretinal surface. The electrode array 110 is electrically coupled by a cable 112, which can pierce the sclera and be electrically coupled to an electronics package 114 external to the sclera. Electronic package 114 includes the RF receiver and electrode drivers.

The electronics package 114 can be electrically coupled to a secondary inductive coil 116. In one aspect, the secondary inductive coil 116 is made from wound wire. Alternatively, the secondary inductive coil may be made from a thin film polymer sandwich with wire traces deposited between layers of thin film polymer. The electronics package 114 and secondary inductive coil 116 are held together by a molded body 118. The molded body 118 may also include suture tabs 120. The molded body narrows to form a strap 122 which surrounds the sclera and holds the molded body 118, secondary inductive coil 116, and electronics package 114 in place. The molded body 118, suture tabs 120 and strap 122 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the secondary inductive coil 116 and molded body 118 are oval shaped, and in this way, a strap 122 can better support the oval shaped coil.

The entire implantable portion 100 is attached to and supported by the sclera of a subject. The eye moves constantly. The eye moves to scan a scene and also has a jitter motion to prevent image stabilization. Even though such motion is useless in the blind, it often continues long after a person has lost their sight. Thus, in one embodiment of the present disclosure, the entire implantable portion 100 of the prosthesis is attached to and supported by the sclera of a subject. By placing the device under the rectus muscles with the electronics package in an area of fatty tissue between the rectus muscles, eye motion does not cause any flexing which might fatigue, and eventually damage, the device.

FIG. 5 shows a side view of the implantable portion of the retinal prosthesis, in particular, emphasizing the fan tail 124. When the retinal prosthesis is implanted, it is necessary to pass the strap 122 under the eye muscles to surround the sclera. The secondary inductive coil 116 and molded body 118 must also follow the strap under the lateral rectus muscle on the side of the sclera. The implantable portion 100 of the retinal prosthesis is very delicate. It is easy to tear the molded body 118 or break wires in the secondary inductive coil 116. In order to allow the molded body 118 to slide smoothly under the lateral rectus muscle, the molded body is shaped in the form of a fan tail 124 on the end opposite the electronics package 114. Element 123 shows a retention sleeve, while elements 126 and 128 show holes for surgical positioning and a ramp for surgical positioning, respectively.

In order to further understand the effects of retinal stimulation, others have applied sophisticated models for temporal processing of light stimuli in the in vitro retina. However, there are some clear distinctions between in vivo studies of implanted subjects and in vitro physiological research. In the present disclosure, the behavioral research will be studied, as opposed to electrophysiology of the in vitro retina, and study the behaviors of awake humans as opposed to an animal model. In addition, a degenerated retina and not a normal, healthy retina will be studied. For example, in RP, retinal degeneration is not simply a loss of photoreceptors. RP patients suffer a loss of other cell types as well, along with significant reorganization and possible changes in circuitry and cell function. As one might surmise, the degenerated retinal system is likely to have different temporal properties than a normal retina.

In the present disclosure, in order to determine how human visual perception depends on the timing of electrical stimulation, a temporal integration was studied during electrical stimulation. The objectives of this include: (1) determination of the potential neurophysiological elements underlying visual perception; and (2) development of a linear-nonlinear model of the temporal integration dynamics of electrical stimulation. It is of interest to understand temporal integration properties because it is thought that this information will help to generate the most effective stimulation patterns. The first step is to look at how visual perception depends on the timing of electrical stimulation patterns.

Figure 6:
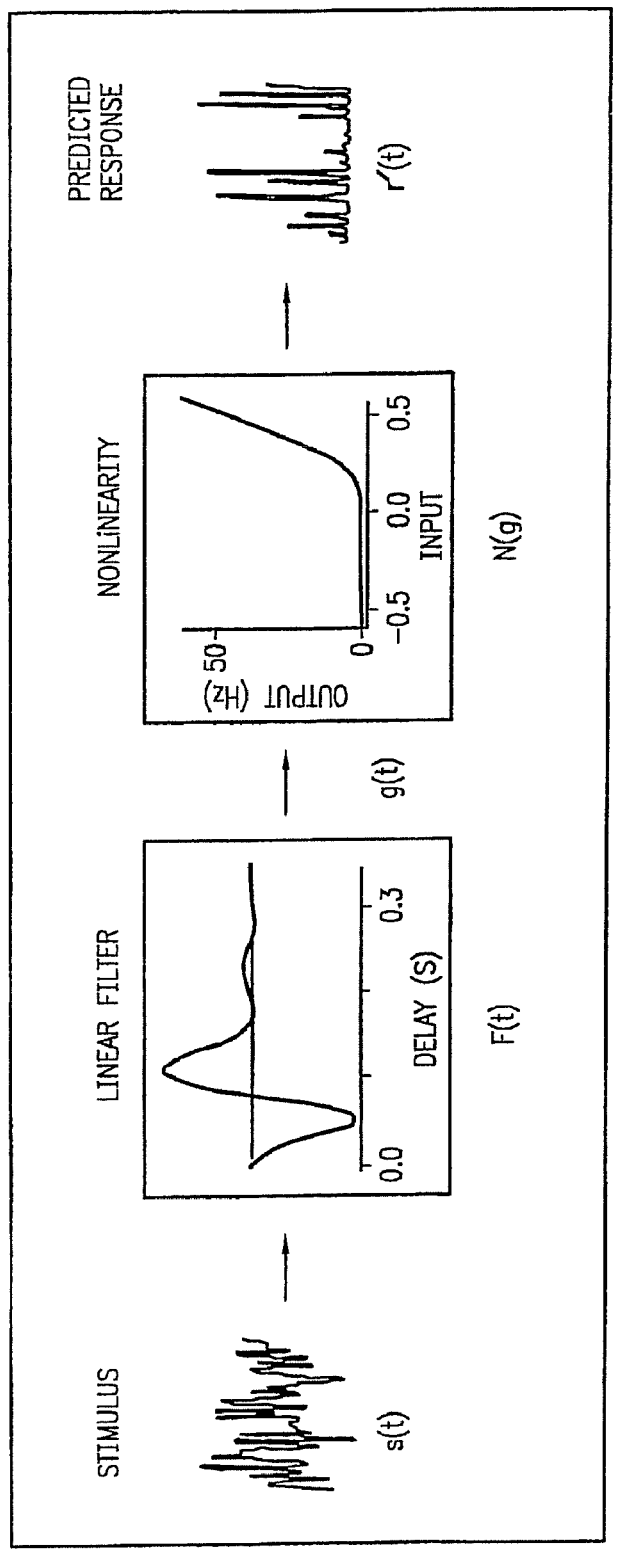
FIG. 6 is a graph showing linear-nonlinear models can predict retinal firing to light stimuli.

FIG. 6 shows a graph of how linear-nonlinear models can predict retinal firing to light stimuli. As noted above, there are models in the art that evaluate the early visual system's response to light stimuli. One example is a model of temporal contrast adaptation in retinal ganglion cells, where the resulting spike train can be predicted based solely upon the light stimulation input (Chander, D. and E. J. Chichilnisky (2001), *Journal of Neuroscience* 21(24): 9904-16; Kim, K. J. and F. Rieke (2001), *J Neuroscience* 21(1): 287-99; Baccus, S. A. and M. Meister (2002), *Neuron* 36(5): 909-19.)

The linear/nonlinear model aides in the prediction of ganglion cell responses to light stimuli, wherein a light flicker stimulus is convolved with a linear filter with a particular time constant. The output of this convolution is then passed through an expanding nonlinearity to ultimately predict the neural response. To evaluate whether such a model is able to predict the perceptual response to electrical stimulation, and how the temporal properties differ when using electrical stimulation rather than light stimulation, perceptual threshold is observed as a function of pulse width.

Figure 7:
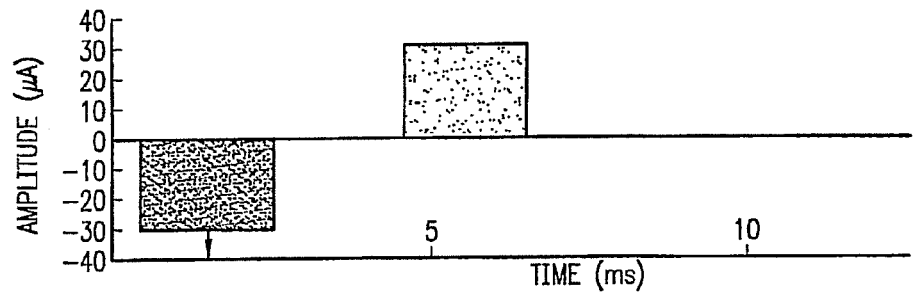
FIG. 7 is a graph showing the effect of pulse duration.

FIG. 7 shows a graph of a biphasic pulse. In accordance with FIG. 7, the stimuli are single, biphasic, cathodic-first, charge-balanced pulses, wherein the pulse width varied between 0.075 milliseconds (ms) and 4 ms, per phase. Anodic pulses are approximately fifty percent as effective as cathodic pulses, thus the anodic pulses are not necessary to consider (Jensen, R. J., O. R. Ziv, et al. (2005), *Invest Opthalmol Vis Sci* 46(4): 1486-96).

Furthermore, the anodic pulses are considered to be far less effective at driving a response in the in vitro retina. This is the result of the orientation of the stimulating electrode relative to the ganglion cell. In this configuration, the negatively-charged cathodic pulse 'pulls' the positive cations within the cell towards the axon hillock, where there is the highest concentration of voltage-gated channels. Therefore, for the method according to the present disclosure, the anodic phase should not be considered when it comes to evaluating the biphasic pulse and its influence on perception.

Figure 8:
FIG. 8 is a graph showing a method for determining visual perceptual threshold.
Figure 8:
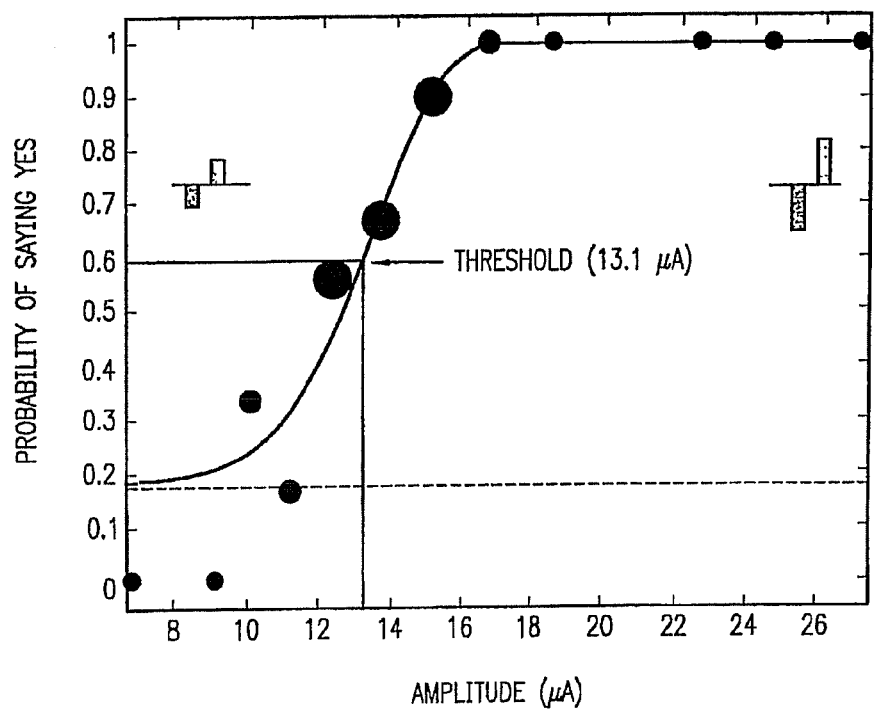

FIG. 8 shows a graph of a method for determining visual perceptual threshold, wherein the threshold was determined as follows. Subjects were exposed to a series of stimuli using a yes-no paradigm wherein half the trials contained no stimulus. The subjects reported whether the trial contained a stimulus or not. The current amplitude was varied using a 3 up, 1 down staircase. In other words, if the subjects got 3 correct answers in a row the subsequent current signal was made more difficult by decreasing the current a step. Likewise, if the subject answered incorrectly, the subsequent current signal was made easier by increasing the current by one step.

The curve shown in FIG. 8 is an example of a generated psychometric function, which was used to analyze the behavioral data. The x-axis is the current amplitude and the y-axis is the probability that the subject saw the stimulus, 1 being that the subject saw it every time at that particular current. The black dots are the subject/patient responses for a specific stimulus condition (a specific current amplitude), with the larger dots representing a greater number of trials at that condition. As is shown in FIG. 8, there is a dramatic shift in performance between 10 uA and 16 uA. After adjusting the curve to the false alarm rate, the curve was fit with a Weibull function and the 50% point was the determined threshold. The Weibull function allows for many different distributions. This function is a common cumulative distribution that is frequently used for life data because its slope parameter can be adjusted to allow the curve to represent different distributions.

Figure 9:
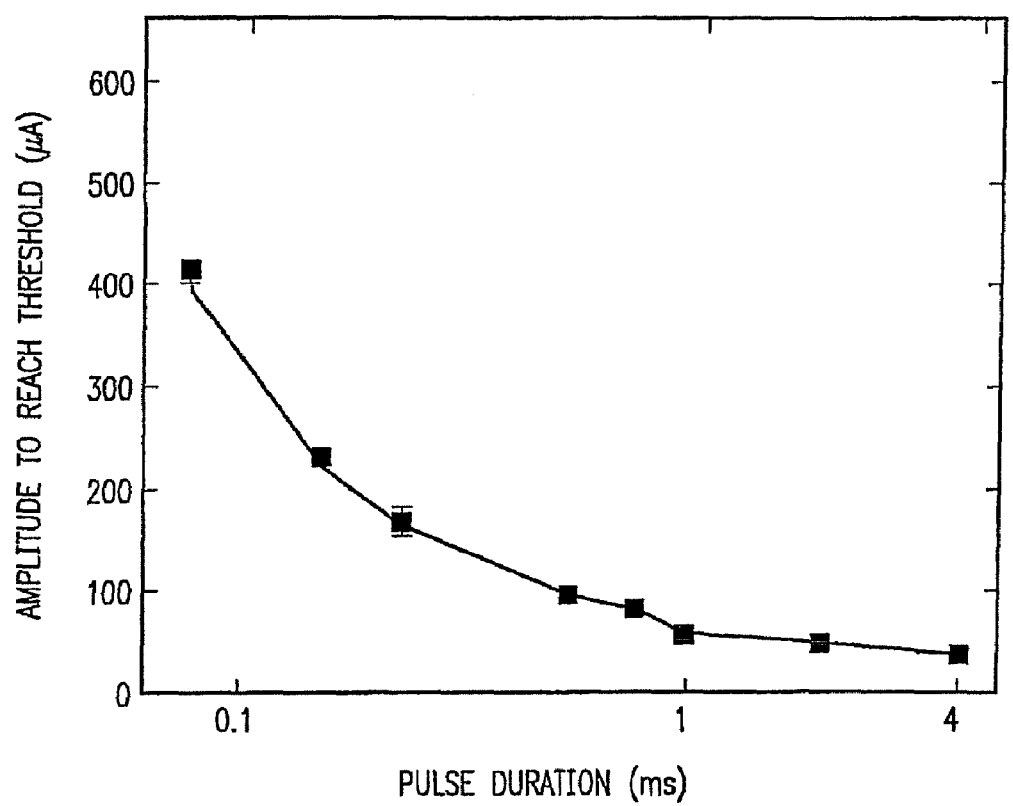
FIG. 9 is a graph showing threshold as a function of pulse width.

FIG. 9 is graph showing threshold as a function of pulse duration or width. FIG. 9 is an example curve (typical of data from 10 electrodes, 2 subjects). Data can be modeled using a simple leaky integrator model. A leaky integrator model represents the accumulation and dissipation of some input (e.g. electric current or charge) that accumulates and dissipates with a specific rate that depends on the value of the time constant. Across all data in FIG. 9, time constants of <1 ms are found, which is consistent with chronaxie values for ganglion cell integration periods (Jensen et al., 2005). The pulse width is on the x-axis varying between 0.075 ms and 4 ms, and the y-axis is the amplitude to reach threshold. The eight boxes shown in the figure represent measured thresholds at their corresponding pulse widths. So, for example, at 0.075 ms, it requires approximately 425 microAmperes ($\mu A$) of current for the patient to be able to see that stimulus 79% of the time. The data show that as the pulse width is increased, there is a decrease in current amplitude needed to reach the threshold. The black line, represents the current model and the fit estimation of this particular data set. Additionally, this data can be fit using a simple leaky integrator model (Kandel, E. R., J. H. Schwartz, et al. (1991). Principles of Neural Science. Norwalk, Conn., Appleton & Lange) having a single free parameter (tau or time constant) that represents the integrative behavior of the system.

Figure 10C:
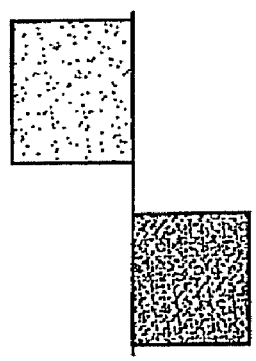
FIGS. 10A-10C are graphs showing the varying integration rates of different cell types.
Figure 10B:
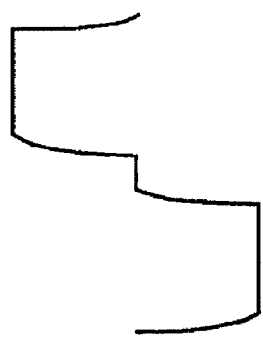
Figure 10A:
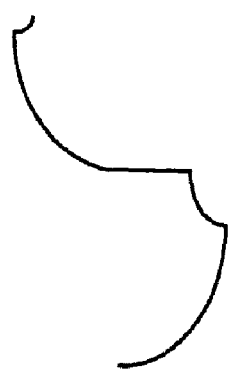

FIGS. 10A-10C show that different cell types integrate charge at different rates with cathodic phases in grey and anodic phases in black. FIG. 10 also shows how a leaky integrator model would integrate a biphasic pulse (FIG. 10A) using a short (FIG. 10B) and long (FIG. 10C) time constant. FIG. 10A represents an input stimulation pattern (biphasic pulse). FIG. 10B represents a fast integrator response to the input, typical of ganglion cells. FIG. 10C represents a slow integrator response, typical of bipolar cells.

For further example, one can imagine two different biphasic pulses that differ in their pulse width, where one is relatively long and the other is short. If a leaky integrator model is applied with fast temporal properties, the response curve follows the shape of the input reasonably well. On the other hand, if the model integrates more slowly, the response is more sluggish, as represented in FIG. 10C by the shallower slope of the response curve. In fact, if the biphasic pulse is short, the amplitude of the response curve is greatly diminished. Applying this concept to the physiology of Jensen (Jensen et al., 2005) and Fried (Fried, S. I., H. A. Hsuch, et al. (2006), *J Neurophysiol* 95(2): 970-8) who reported that integration periods of ganglion cells are substantially faster than those of either bipolar or amacrine cells, suggests that it may be possible to exclusively activate ganglion cells with shorter pulse widths.

Figure 11:
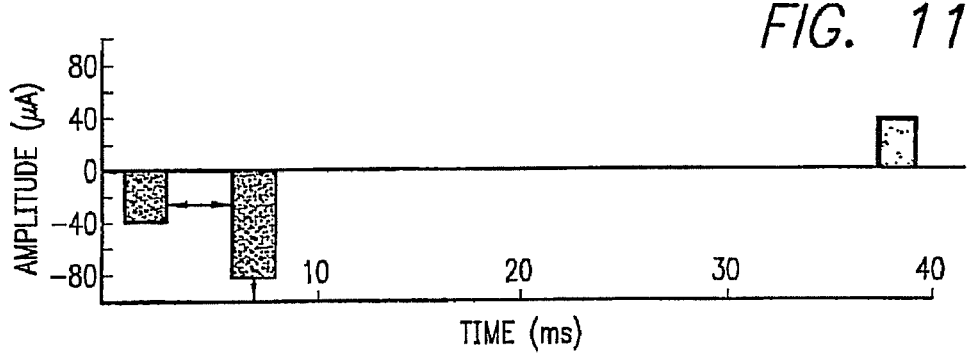
FIG. 11 is a graph showing summation across pulse pairs.

Another approach to evaluating the temporal integration of the system is by looking at how two separate pulses sum in time. FIG. 11 is a graph showing summation across pulse pairs. Stimuli were 0.075 ms pseudo-monophasic cathodic pulses. The first pulse had fixed current amplitude (sub-threshold). The second pulse followed with a variable delay (0.15-12 ms). The experiment, illustrated by FIG. 11, evaluates the summation across pulse pairs. In other words, the experiment determines how the first pulse, (i.e. the conditioning pulse) contributes to the threshold response of the second pulse, (i.e. the test pulse). The stimuli were pseudo-monophasic because, for obvious safety reasons, a charge-balanced anodic phase is included, as shown by the positive pulse to the right of FIG. 11. The difference here is that the anodic pulses were presented later in time by about 30 ms.

Figure 12:
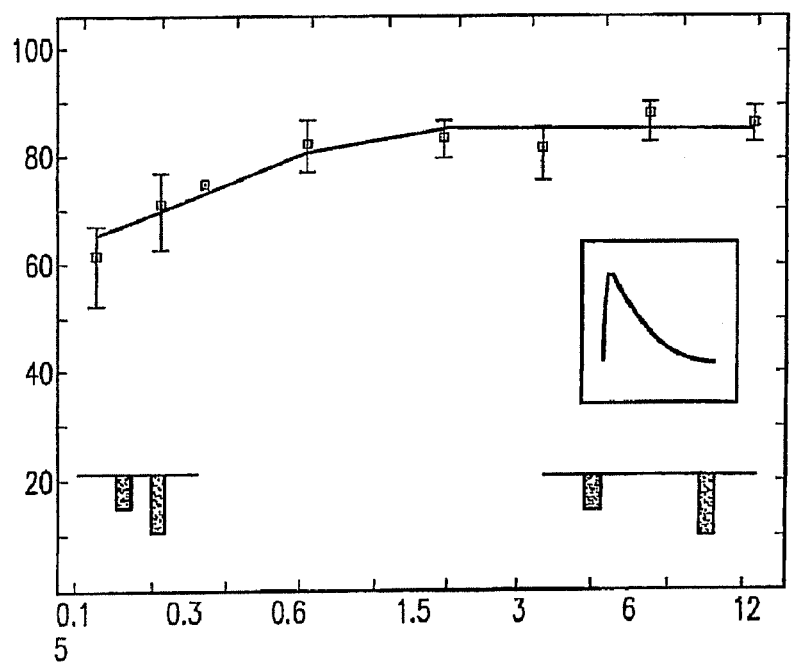
FIG. 12 is a graph showing threshold for pulse pairs.

FIG. 12 is a graph showing threshold for pulse pairs. The graph derives from a data set of 8 different electrodes across two subjects. The time constants were the same (<1 ms) as the single pulse data are consistent with ganglion cell stimulation. With pulse pair summation it was determined that there is a critical window of integration.

In particular, the x-axis of FIG. 12 shows the delay between pulse pairs, and the y-axis is the amplitude to reach threshold. The critical window of integration was observed to be somewhere short of one millisecond. More specifically, looking at the portion of the curve before the 1 ms delay value, a short increase in delay provides a large increase in amplitude to reach threshold. On the other hand, after the one millisecond point, the curve asymptotes and the current value at which it asymptotes is the same as that for a single biphasic pulse. This observation means the following: first, that the secondary anodic phase has no influence on threshold, and secondly, that the integration period is very short. If these data were fitted to a leaky integrator model, time constants would be similar to those of ganglion cells.

Therefore, all the data shown thus far provide a strong indication of how simple and very short stimuli are integrated over time. However, a further objective of the present disclosure is to determine continuous stimulation in order to provide visual information to improve navigation and visual recognition. In view of this further objective, one or two electrical pulses are not enough.

Figure 13:
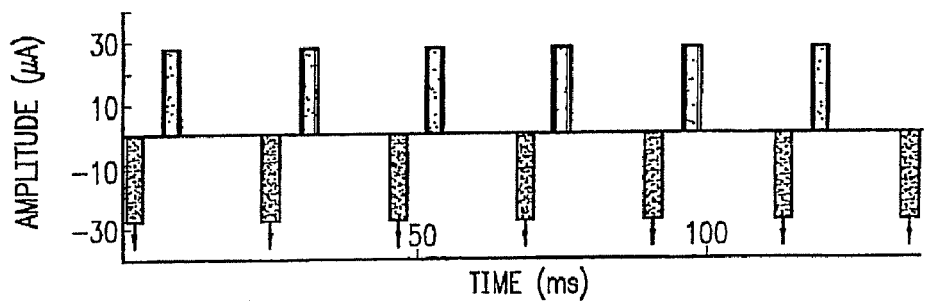
FIG. 13 is a graph showing fixed duration pulse trains.

FIG. 13 is a graph showing a fixed duration pulse train, i.e. a series of multiple pulses where every pulse has the same width. In particular, in order to determine how multiple pulses integrate over time, stimuli were fixed duration pulse trains of 200 milliseconds. Pulses were either 0.975 or 0.075 milliseconds in duration, and frequency varied between 5 Hz and 225 Hz. Amplitude of all pulses in the train varied simultaneously to find threshold. In other words, the amplitude of each pulses within the pulse train increased and/or decreased at the same time.

Figure 14:
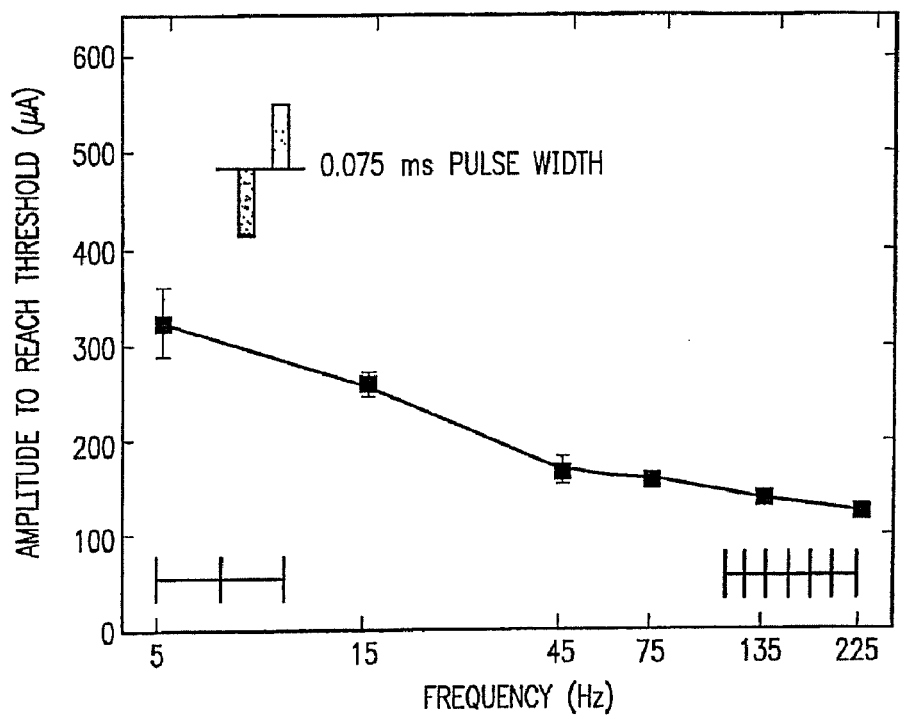
FIG. 14 is a graph showing threshold for fixed duration pulse trains of 0.075 ms pulse width.
Figure 15:
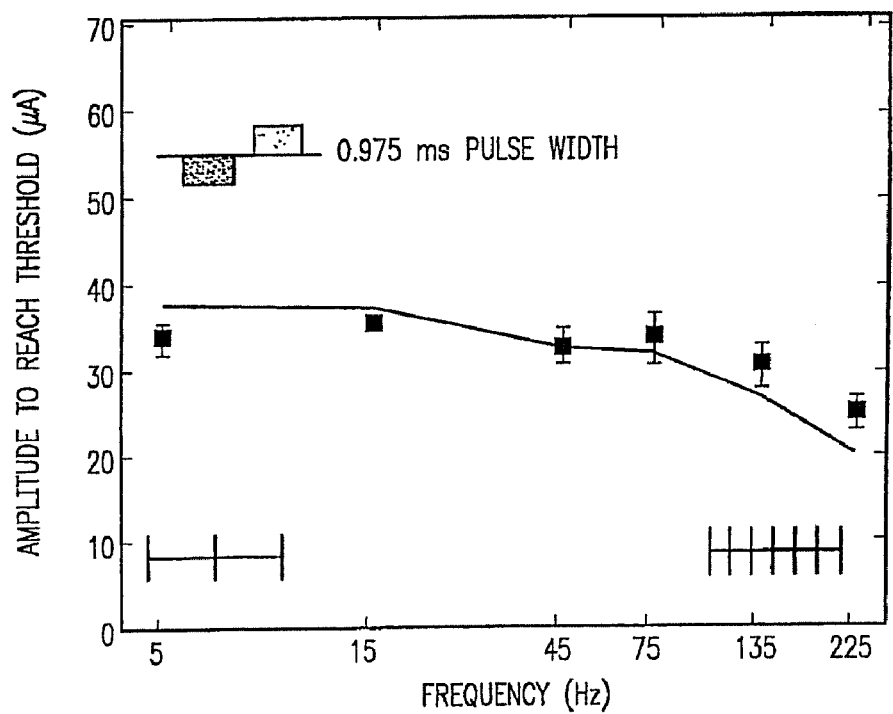
FIG. 15 is a graph showing threshold for fixed duration pulse trains of 0.0975 ms pulse width.

FIGS. 14 and 15 show graphs indicative of threshold for fixed duration pulse trains like the one shown in FIG. 9.

It has already been discussed above that the reduction in the amount of current needed to reach the threshold is due to interactions between pulses. FIG. 14 and FIG. 15 show that the decrease in threshold is driven by the frequency of the pulses.

The graph of FIG. 14 refers to data coming from pulse trains having widths (duration of each pulse) of 0.075 ms. On the other hand, the graph of FIG. 11 refers to data coming from pulse trains having widths of 0.975 ms. In both cases, the x-axis frequency range is the same, i.e. 5 Hz to 225 Hz. However, there is a significant difference between the amplitude values to reach threshold of the two Figures. The values of FIG. 14 (between about 300 and about 100 microAmperes) are an order of magnitude greater than the values of FIG. 15 (between about 40 and about 20 microAmperes). In both graphs, solid lines have been added to show the behavior of the model.

The reason for the different result is the difference in pulse width (0.075 ms vs. 0.975 ms). In particular, as the pulse width is increased, less current is required to drive the system to threshold, as also previously discussed.

Therefore, it appears that a decrease in threshold is a function of frequency of the pulses. However, the response to pulse trains is dynamic, and the resulting pulse train data cannot be fitted to a leaky integrator model, as there are interactions between pulses that go beyond that of the model. Also, there is one potential confound with the pulse train data, and that is that since fixed duration pulse trains are being used, in order to change the frequency an increase in the number of pulses is required. For example, at 15 Hz, 3 pulses are used, and at 225 Hz, 45 pulses are used.

In order to determine if a decrease in threshold is a function of frequency or a function of the number of pulses, or a function of both, the applicants have examined the relationship between frequency and the number of pulses.

Figure 16A:
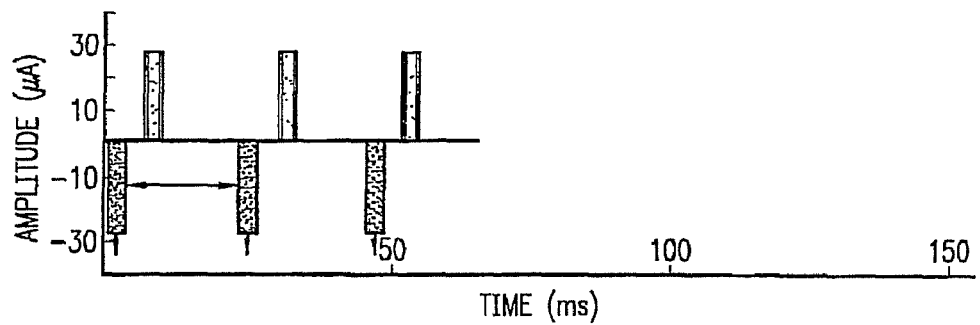
FIGS. 16A, 16B are graphs showing threshold for variable duration pulse trains.
Figure 16B:
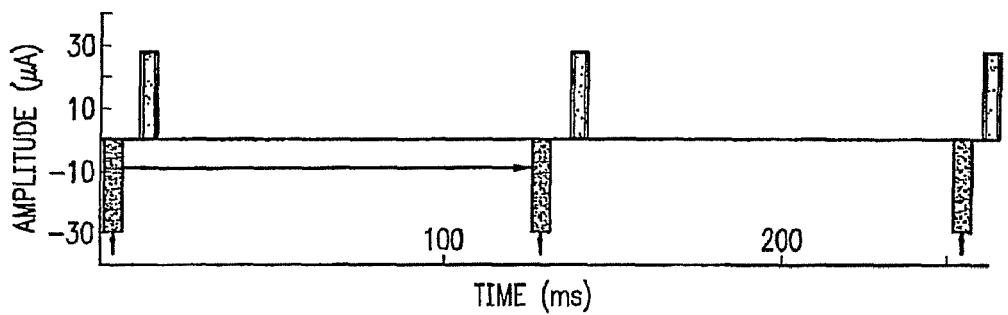

FIGS. 16A and 16B are graphs showing threshold values for variable duration pulse trains. In this example, the stimuli consisted of pulse trains of 2, 3, and 15 pulses (where the 2 and 3 pulses examples are shown in FIG. 12). The frequency of these pulse trains was varied by changing the delay between the biphasic pulses. The delay varied from 0.075 ms to 300 ms, corresponding to a range of frequencies between approximately 3000 and approximately 3 Hz. As with the fixed duration pulse train data, perceptual threshold was measured by varying the amplitude of all the pulses within the pulse train simultaneously. In other words, the amplitude of each pulse within the pulse train increased and/or decreased at the same time.

Figure 17:
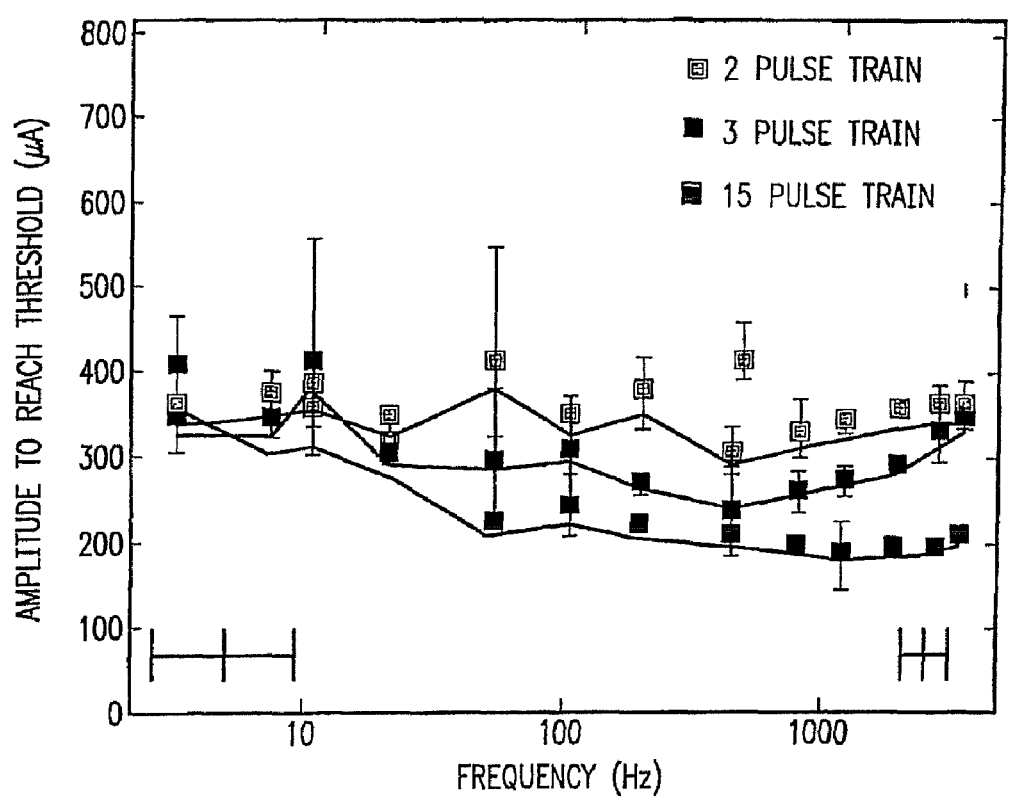
FIG. 17 is a graph showing the relationship between threshold, frequency and the number of pulses.

FIG. 17 is a frequency vs. amplitude-to-reach-threshold graph similar to the ones shown in FIGS. 10 and 11, where relationship between frequency and number of pulses is also shown. Here, the x-axis is represented in a logarithmic scale. Three curves are shown. The curve on top corresponds to a 2 pulse train. The curve in the middle corresponds to a 3 pulse train. The curve on the bottom corresponds to a 15 pulse train. Differences in behavior between the different numbered pulse trains do not appear until frequencies above about 20 Hz (about 50 Hz), wherein as the number of pulses is increased, there is a decrease in necessary current to reach threshold The three curves are separated by 300 ms at the lowest frequency (3 Hz) and by 0.075 ms at the highest frequency (3333 Hz). It should be noted that these curves, as with all the data presented, are generated using a Monte Carlo simulation.

The data of FIG. 17 show that there is no statistical difference in perceptual threshold for all three of the different numbered pulse trains. That is, presenting two pulses at 20 Hz or presenting fifteen pulses at 20 Hz results in the same perceptual threshold, and therefore, perceptual threshold becomes independent on pulse timing. This is more clearly represented when the data in the fifteen pulse trains is averaged over six electrodes for two patients. Looking at the higher frequencies, there is no statistical change in threshold as a function of frequency, representing independence on timing but a dependence on pulse number. The lower frequencies, as noted above, are independent of pulse number, but have a clear relationship to pulse timing.

Figure 18:
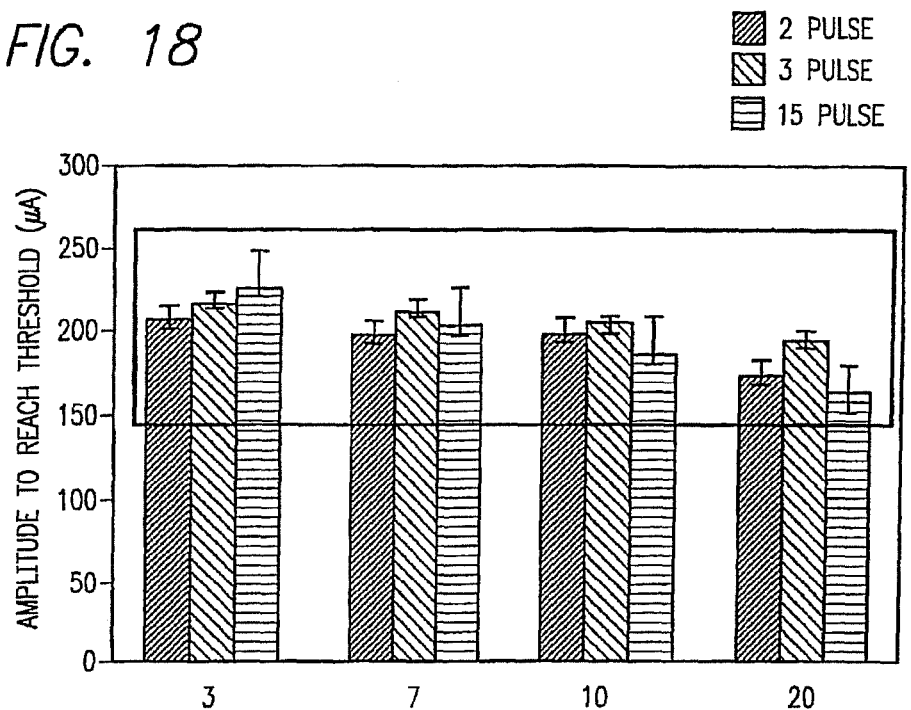
FIG. 18 is a graph showing that the thresholds of pulse trains with frequency below 50 Hz are independent of pulse number.

FIG. 18 is a graph showing that thresholds for pulse trains with frequencies below about 50 Hz are independent of the number of pulses. The graph refers to data for thresholds for the two (grey bar), three (diagonal-lined bar) and fifteen (horizontal-lined bar) pulse train data of FIG. 17, averaged over six electrodes and over two subjects, plotted for frequencies of 3, 7, 10 and 20 Hz, wherein the error bars represent the standard error. Although there may be slight statistical differences between these data, and there is a trend downward as a function of frequency for the fifteen pulse data, the statistical differences between the two, three, and fifteen pulse data, when compared at each frequency, are very similar. This similarity between pulse trains suggests that perceptual thresholds of the input are independent of pulse number. However, for the fifteen pulse data, a dependency on pulse timing occurs at lower frequencies.

Figure 19:
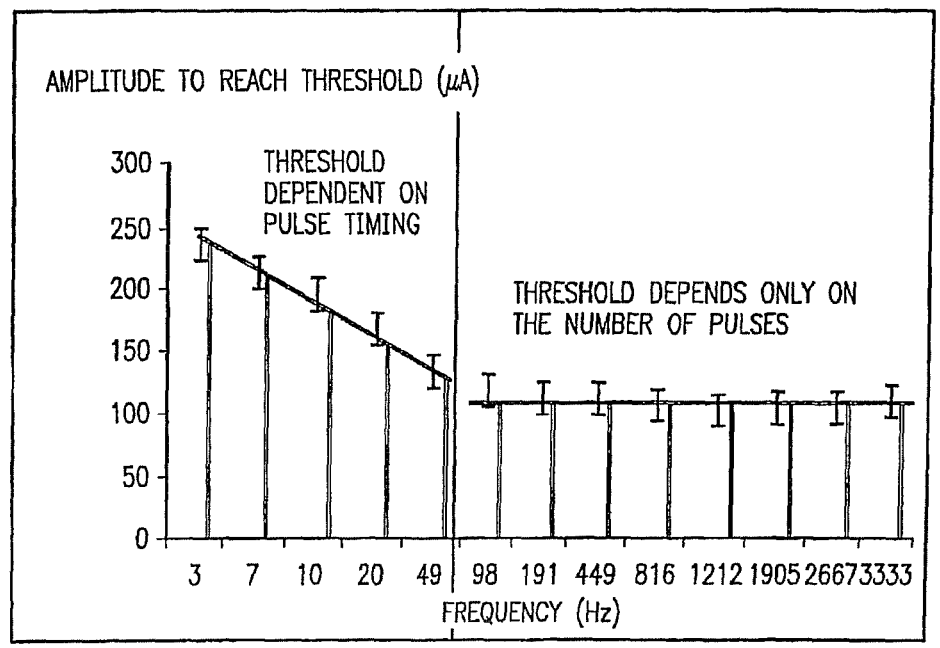
FIG. 19 is a graph showing that thresholds for pulse trains with frequencies above 50 Hz are independent of pulse timing.

In view of the data in FIG. 19, and the disclosure that ganglion cells operate in a range that is somewhere below 250 Hz (O'Brien, B. J., T. Isayama, et al. (2002), *Journal of Physiology* 538(Pt 3): 787-802), it is determined that increasing frequencies above this operating ceiling does not supply the system with any additional information about the stimulus because ganglion cells are computationally incapable of processing frequencies in this higher range. In another aspect, if the cortex is thought of as a low pass filter, all the pulses within these higher frequency trains fall within the limits of this integrative window. Thus, if the window of integration of the cortex is on the order of several hundred milliseconds, as long as all the pulses within that train fall within that window (above ~50 Hz), the response will be the same.

Figure 20:
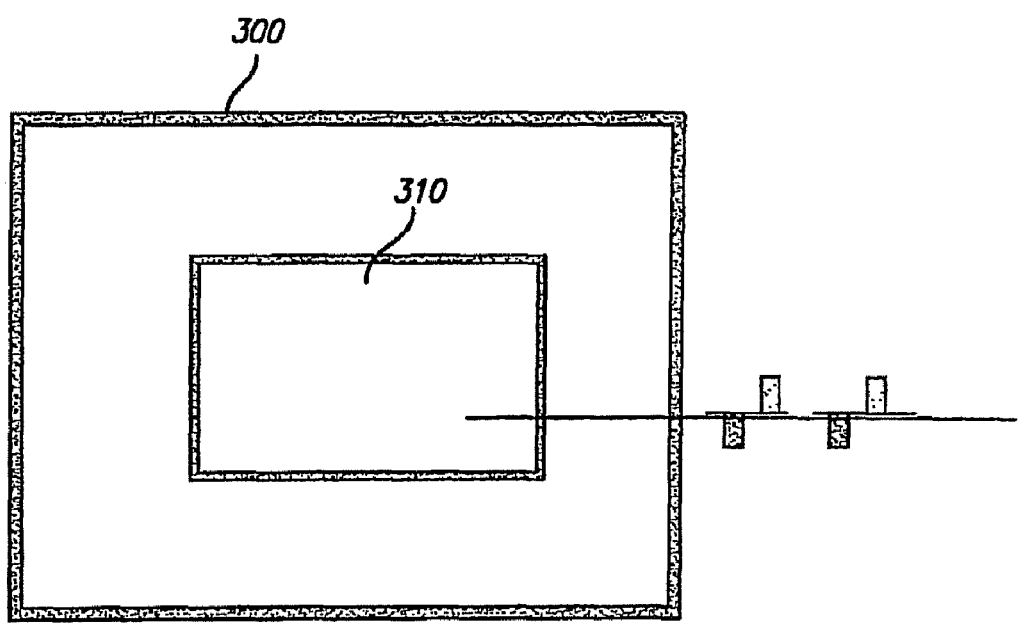
FIG. 20 is a schematic of a retinal stimulation device comprising a stimulation pattern generator.

FIG. 20 shows a stimulation pattern generator 310 which can provide the impulsive electrical signals to implement a determined stimulation pattern from observing a perceived threshold. This stimulation pattern generator can be programmed to provide a pattern of pulse trains having a pulse train frequency and a pulse width. For example, the stimulation pattern generator can be programmed to provide a pulse train having a frequency less than 50 Hz, wherein the pulse width is fixed at 0.075 ms or 0.975 ms. Alternatively the stimulation pattern generator can provide a pulse train having a frequency higher than 50 Hz, wherein the pulse width is variable. As shown, the stimulation pattern generator is connected to a retinal stimulating device 300. An example of a retinal stimulating device is shown in FIGS. 1 and 2.

In summary, a process for designing an apparatus and a method for stimulating neural tissue is provided. The apparatus provides a means for adjusting the RF link to the internal coils, and the method provides the maximum intensity with minimum current by modeling responses to varying stimulation parameters including frequency, pulse width, and pattern of pulse series (trains).

Accordingly, what has been shown is an apparatus and method for stimulating neural tissue for improved response to brightness. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A retinal stimulation method, comprising:
   generating a stimulation pattern by stimulating a retina of a patient with an impulsive electrical pulse train signal including multiple pulses less than 200 millisecond apart;
   generating additional stimulation patterns by varying parameters of the stimulation pattern; and
   determining how visual perception depends on the generated stimulation patterns by observing perceptual threshold as a function of features of the impulsive electrical signal, and applying a leaky integrator model based on a stimulus energy with time constants less than 1 ms to predict thresholds.

2. The method of claim 1 wherein the impulsive electrical signal comprises biphasic pulses.

3. The method of claim 2, wherein width of the biphasic pulses varies between 0.075 ins and 4 ms.

4. The method of claim 1, wherein said determining how visual perception depends on the generated stimulation pattern takes into account effects of cathodic pulses and does not take into account effects of anodic pulses when evaluating influence of biphasic pulses on perception.

5. The method of claim 1, wherein said determining how visual perception depends on the generated stimulation pattern comprises evaluating amplitude to reach threshold in function of pulse width to find that current amplitude to reach threshold decreases as pulse duration increases.

6. The method of claim 5, wherein the pulse width is fixed to be either 0.075 ms or 0.975 ms.

7. The method of claim 5, wherein pulse width is made variable between 0.075 ms and 4 ms.

8. The method of claim 5, further comprising a delay between pulses, wherein said delay is variable and said variable delay varies between 0.075 ms and 300 ms.

9. The method of claim 1, wherein said determining how visual perception depends on the generated stimulation pattern comprises evaluating summation across at least one pulse pair in function of amplitude to reach threshold to determine how a first pulse of the at least one pulse pair contributes to a threshold response of a second pulse of the at least one pulse pair.

10. The method of claim 9, wherein the first pulse comprises a fixed current amplitude and the second pulse follows with a variable delay.

11. The method of claim 10, further comprising a delay between the first and second pulse, wherein said delay is variable and said variable delay varies between 0.075 ins and 300 ms.

12. The method of claim 9, wherein the at least one pulse pair comprises a pulse frequency and said pulse frequency varies between 5 Hz and 225 Hz.

13. The method of claim 1, wherein the determining how visual perception depends on the generated stimulation pattern comprises evaluating amplitude to reach threshold in function of pulse train frequency to find that current amplitude to reach threshold decreases as pulse train frequency increases.

14. The method of claim 13, further comprising evaluating whether decrease of amplitude to reach threshold also depends on number of pulses.

15. The method of claim 14, wherein at a pulse train frequency of less than 50 Hz, the threshold depends on a delay between pulses.

16. The method of claim 14, wherein at a frequency of greater than 50 Hz, the threshold depends on the number of pulses and is independent of frequency.

17. The method of claim 13, wherein said evaluating amplitude to reach threshold in function of pulse train frequency comprises evaluating plural pulse trains.

18. The method of claim 17, wherein the plural pulse trains comprise a first pulse train with two pulses, a second pulse train with three pulses, and a third pulse train with fifteen pulses.

19. The method of claim 17, further comprising a delay between pulses of each pulse train wherein the delay varies between 0.075 ms to 300 ms.

20. The method of claim 1, wherein the method is applied to patients with a degenerated retina.

21. The method of claim 1, wherein the features of the impulsive signal include at least one between: pulse width, pulse amplitude, and pulse frequency.

22. The method of claim 1, wherein one of said parameters is frequency.

23. The method of claim 1, wherein one of said parameters is pulse width.

24. The method of claim 1, wherein one of said parameters is pattern of pulse train.

25. The method of claim 1, wherein the pulse trains include multiple pulses spaced to cause integration of the multiple pulses by the target cell.

26. The method of claim 1, wherein the time constant is consistent with chronaxie values for ganglion cell integration periods.

* * * * *

UNITED STATES PATENT AND TRADEMARK OFFICE
CERTIFICATE OF CORRECTION

PATENT NO. : 8,311,634 B2  
APPLICATION NO. : 11/818373  
DATED : November 13, 2012  
INVENTOR(S) : Alan Matthew Horsage et al.

Page 1 of 1

It is certified that error appears in the above-identified patent and that said Letters Patent is hereby corrected as shown below:

Column 12, Claim 19, line 19, delete "17" and replace with -- 18 --.

Signed and Sealed this
Twenty-fifth Day of December, 2012

David J. Kappos
*Director of the United States Patent and Trademark Office*